United States Patent [19]

Modena et al.

[11] 4,025,468
[45] May 24, 1977

[54] HALOGENATED PHOSPHORIC ESTERS AND FLAME-PROOFING COMPOSITIONS FOR POLYMERIC MATERIALS BASED THEREON

[75] Inventors: Mario Modena; Roberto Bisel, both of Bollate, Italy

[73] Assignee: Montedison Fibre S.p.A., Milan, Italy

[22] Filed: Apr. 11, 1975

[21] Appl. No.: 567,155

[30] Foreign Application Priority Data

Apr. 12, 1974 Italy .................................. 21366/74

[52] U.S. Cl. .......................... 260/2.5 AJ; 260/928; 260/931; 260/969
[51] Int. Cl.[2] ...................... C07F 9/09; C07F 9/38; C08G 18/06
[58] Field of Search .............. 260/2.5 AJ, 969, 928, 260/931

[56] References Cited

UNITED STATES PATENTS

| 2,807,636 | 9/1957 | Buls et al. ........................... 260/969 |
| 3,027,349 | 3/1962 | Bahr et al. ........................... 260/969 |
| 3,042,701 | 7/1962 | Birum ................................. 260/931 |
| 3,471,592 | 10/1969 | Friedman ........................... 260/931 |
| 3,730,917 | 5/1973 | Hesskamp ..................... 260/2.5 AJ |
| 3,850,859 | 11/1974 | Wortmann et al. ............ 260/2.5 AJ |

OTHER PUBLICATIONS

Gefter—Organophosphorus Monomers & Polymers (Assoc. Techn. Services) (Glen Ridge, N.J.), p. 37 (1962).

*Primary Examiner*—Donald E. Czaja
*Assistant Examiner*—H. H. Fletcher

*Attorney, Agent, or Firm*—Hubbell, Cohen, Stietel & Gross

[57] ABSTRACT

Polyurethanes such as polyol based polyurethanes are rendered flame resistant by incorporating therein 1–25 parts per hundred parts by weight of a mixture of halogenated phosphoric esters consisting essentially of at least two compounds of the formula:

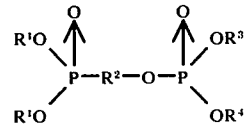

wherein $R^1$ is a $C_1$–$C_3$ alkyl or an $R^2X$ group, $R^2$ is a $C_2$–$C_3$ alkylene group and $R^3$ and $R^4$ are independently selected from the group consisting of $R^2X$, wherein X is H, or a halogen;

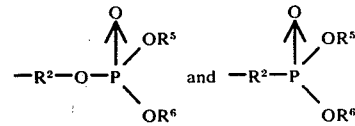

wherein $R^5$ and $R^6$ are independently selected from the group consisting of $R^1$, $R^2X$ and

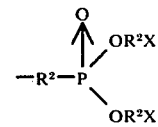

7 Claims, No Drawings

HALOGENATED PHOSPHORIC ESTERS AND FLAME-PROOFING COMPOSITIONS FOR POLYMERIC MATERIALS BASED THEREON

CROSS REFERENCE TO RELATED APPLICATIONS

None.

BACKGROUND OF THE INVENTION

1. Field of the Invention

This invention relates to halogenated phosphoric esters and to flame-proofing compositions for polymeric materials such as polyurethanes and polyesters, based on such halogenated phosphoric esters.

2. The Prior Art

It is, of course, known that to improve the flame resistance of polymeric materials, flame-proofing additives, i.e., products which are capable of rendering the polymeric materials fire-proof or self-extinguishing or at the very least, capable of reducing the combustion rate thereof are added to the polymeric materials.

For some time now, certain halogenated phosphoric esters have been proposed for utilization as flame-proofing additives for polymeric materials of various types, including particular polyesters and polyurethanes.

It is known that polyurethanes, to which have been added certain of the known halogenated phosphoric esters, while exhibiting good flame resistance characteristics, may sometimes be subject, after ageing, to mechanical and thermal degradation phenomena, which seriously limit the practical utilization of such treated polyurethanes.

Moreover, certain of the known halogenated phosphoric esters, when incorporated into polyurethanes tend somehow to migrate towards the outside of the material into which they had been incorporated and then to volatilize therefrom, as a result of which their permanence characteristics are not completely satisfactory.

Accordingly, it is an object of the present invention to provide halogenated phosphoric esters suitable for use as flame-proofing additives for various types of polymers and which are free of the above-mentioned disadvantages.

SUMMARY OF THE INVENTION

According to the invention, there is provided a new class of halogenated phosphoric esters, and a process for preparing same. These halogenated phosphoric esters are superior in their flame-proofing and self-extinguishing characteristics to that of conventional flame-proofing additives, including certain known halogenated phosphoric esters.

The halogenated phosphoric esters according to the present invention are a mixture of two or more compounds having the general formula (I):

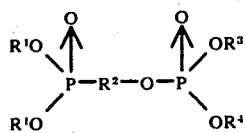

wherein $R^1$ is a $C_1$–$C_3$ alkyl group, or an $R^2X$ group, $R^2$ is a $C_2$–$C_3$ alkylene group and $R^3$ and $R^4$ are independently selected from the group consisting of —$R^2X$, wherein X is hydrogen or a halogen, such as chlorine or bromine;

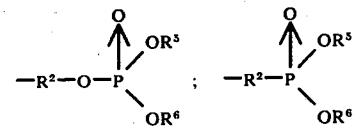

wherein $R^5$ and $R^6$ are independently selected from the group consisting of $R^1$ and —$R^2X$; and

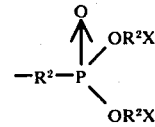

The compounds according to the invention and having the formula (I) are prepared by reacting at a temperature of 140° C to 220° C, for a period of 2–24 hours, a trialkylphosphite of the formula $P(OR^1)_3$ and a tris(haloalkyl)phosphate of the formula $PO(OR^2X)_3$, wherein $R^1$, $R^2$ are as defined above, and X is, in this case, a halogen, such as chlorine or bromine. The obtained products contain 2 to 6 phosphorus atoms and 0–3 halogen atoms per molecule.

Particularly preferred compounds that are well suited for the invention are the mixtures of halogenated phosphoric esters formed by the reaction between triethylphosphite and tris($\beta$-chloroethyl)phosphate, and which are essentially made up of two or more compounds having the general formula (I) wherein $R^1$ is —$C_2H_5$ and $R^2$ is —$C_2H_4$— and $R^3$ and $R^4$ are as defined above.

More particularly, the main components of such mixtures, are compounds of formula (I), wherein $R^1$ is —$C_2H_5$ and $R^2$ is —$C_2H_4$—; $R^3$ and $R^4$ being different in each of the compounds of the mixture as follows:

a) $R^3 = R^4 = $ —$CH_2$—$CH_2Cl$ (mass=386)

b) $R^3$ is —$CH_2$—$CH_2$—$Cl$ and (mass=488)

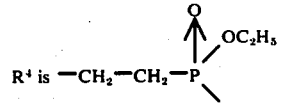

c) (mass=590)

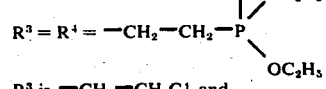

d) $R^3$ is —$CH_2$—$CH_2Cl$ and (mass=572)

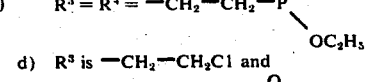

e) $R^3$ is —$CH_2$—$CH_2Cl$ and

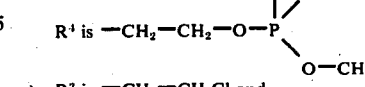

wherein $R^5$ is —$CH_2$—$CH_2Cl$ and (mass=674)

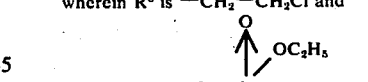

f) $R^3$ is —$CH_2$—$CH_2Cl$ and

-continued

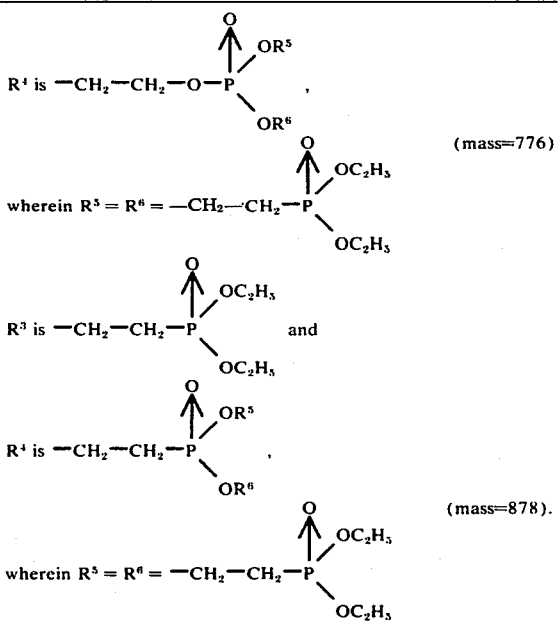

Of course, the ratio among the various components of the mixture of halogenated phosphoric esters according to the invention depends upon the molar ratio of the starting reagents; i.e., the tris(haloalkyl)phosphates and the trialkylphosphites, and particularly, the tris(β-chloroethyl)phosphates and the triethylphosphite, in the sense that, although the product obtained from time to time has a composition that is always substantially identical as to quality and properties, there are variations in the quantitative ratios among the various halogenated phosphoric esters constituting the reaction mixture. Generally, the molar ratio of the reagents is from 1:3 to 3:1.

It has been found that the halogenated phosphoric esters according to the invention may be successfully used as flame-proofing additives for many polymeric materials.

The halogenated phosphoric esters according to the invention are particularly suited for use as flame-proofing additives for foamed polyurethanes and particularly, flexible foamed polyurethanes.

In fact, it has been ascertained that flexible foamed polyurethanes, when admixed with the halogenated phosphoric esters according to this invention in amounts ranging from 1 to 25 parts per 100 parts by weight, and subjected to a combustion test according to the method of ASTM D 1692/68, are self-extinguishing or are characterized by a low combustion rate, in some cases less than 50% of that of polyurethanes not containing flame-proofing additives Furthermore, flexible foamed polyurethanes admixed with the halogenated phosphoric esters of the invention, even if subjected to ageing (according to the method of ASTM D 2406/68) prior to combustion, are characterized by a good flame resistance and are not subject to thermal or mechanical degradation phenomena, as contrasted with foamed polyurethanes admixed with certain of the known flame-proofing based on halogenated phosphoric esters other than those of the invention.

Moreover, the halogenated phosphoric ester mixtures according to the invention exhibit excellent permanence characteristics in flexible foamed polyurethanes, i.e., they remain in the polymeric material and do not volatilize off. This contrasts with certain of the known flame-proofing additives which are known to be lost via volatilization.

The halogenated phosphoric esters according to the invention may be advantageously employed in admixture with other flame-proofing additives for polymers (in particular for polyurethanes), especially with bromine- or chlorine-containing additives.

The halogenated phosphoric esters of the present invention are particularly suited to be utilized as flame-proofing additives for flexible foamed polyurethanes, prepared according to conventional methods starting from polyols, isocyanates and other components of a type well known to those skilled in the art.

A particularly suitable group of polymeric materials consists of flexible foamed polyurethanes prepared from:

Straight or branched chain polyethers obtained from ethylene oxide and/or propylene oxide, reacted with glycerin, propandiol, trimethylolpropane, sorbitol and other polyhydroxyl compounds, having an OH number from 20 to 700, preferably from 30 to 60, a functionality between 2 and 6, preferably 2 or 3, and a molecular weight from 200 to 8000, preferably from 3000 to 6000; or formed by reaction of polyesters adipic, sebacic or linoleic dimerized acid and glycols, such as 1,2-ethylene glycol-1,4-butadiol, 1,6-hexandiol, diethylene glycol and/or glycerin, trimethylolpropane, 1,2,6-hexantriol, 1,2,4-butantriol and the like, and having an OH number from 20 to 700, preferably from 2 to 60, and an acidity number lower than 5. A particularly suited product is polydiethylene glycol adipate having an OH number between 35 and 45 and a molecular weight between 1000 and 3000, and organic isocyanates such as toluene diisocyanate, diphenylmethane diisocyanate and other similar compounds; a particularly suited product consists of a mixture of 2,4-toluene diisocyanate with a lesser amount of 2,6-toluene diisocyanate, in the presence of a catalyst such as amines and/or organo-metallic compounds, swelling agents, preferably water and/or chlorofluorohydrocarbons, and further various additives such as surfactants, fillers, modifiers, plasticizers and the like. The equivalent ratio between isocyanates and total active hydrogens (isocyanate index) is between 0.95 and 1.5, preferably between 1 and 1.2; the ratio between isocyanates and water varies from 1.1 to 5, preferably from 1.2 to 2, while the ratio between isocyanates and polyol ranges from 1.1 to 20, preferably from 3 to 10.

The flexible foamed polyurethanes most suitable for use with the halogenated phosphoric esters according to the invention exhibit a density between 10 and 80, preferably between 15 and 65 kg./m³.

DESCRIPTION OF THE PREFERRED EMBODIMENTS

The following examples are given to more clearly illustrate the essential features of the present invention, without, however, being a limitation thereof.

EXAMPLE 1

286.6 g. of tris(β-chloroethyl)phosphate were admixed with 168 g. of triethylphosphite. The resulting mixture in which the components were present in a 1:1 molar ratio was heated to 160° C. and kept at that temperature for 8 hours under intense stirring, in a stream of nitrogen gas which serves to enable easy removal of the volatile products which evolve during the reaction. At the end of the reaction, the following fractions were obtained:

1. 75.1 g. of volatile materials which were condensed in a trap cooled to −78° C., the main components being ethyl chloride and symmetrical dichloroethane; and
2. 367.1 g. of residual products remaining in the reaction vessel.

Fraction (2) was distilled at 120°–125° C. at a pressure of $10^{-2}$ mm. Hg for 3 hours to obtain:

a distilled fraction (3), 77.7 g.

and a residue (4), 289.4 g.

Fraction (3) contained, in addition to other products, the unreacted triethylphosphite, while the residue fraction (4) contained the reaction product and the unreacted tris(β-chloroethyl) phosphate.

To remove the tris(β-chloroethyl)phosphate from residue (4) the residue was distilled in a molecular column at 120° C., $10^{-3}$ mm. Hg with a contact time of 10 to 15 seconds, thus obtaining fraction (5): 93.7 g. of distillate; and fraction (6): 193.5 g. of residue.

Residue (6) had a density of 1.34 at 22° C., a refractive index of 1.4662 at 20° C. and a Brookfield viscosity of 700 cps at 18° C. Upon elemental analysis its %-composition by weight was found to be:

| | | |
|---|---|---|
| carbon | = | 30.4% |
| hydrogen | = | 5.5% |
| phosphorus | = | 17.1% |
| chlorine | = | 13.6% |

NMR analysis of residue (6) revealed the following signals and proton percentages:

| | | |
|---|---|---|
| $CH_3$ | 1.2 ppm | 31.73% |
| $P\ CH_2$ | 2.2 ppm | 7.19% |
| $O-CH_2$ } $ClCH_2$ | 4 ppm | 61.09% |
| Reference: : hexamethyldisiloxane (HMDS). | | |

A portion of residue (6) was separated via thin layer chromatographic techniques and the various fractions obtained were analyzed by a mass spectrograph.

To carry out the chromatographic separation, plates coated with K gel HF (Merck) were used. The eluent was a 9:1 (vol.) mixture of chloroform and ethanol. The presence of individual compounds was detected by iodine vapors and UV light.

To carry out the mass spectrometric analysis, a Hitachi RMU 6E spectrometer operating at an electronic ray energy level of 70 e V was used. For the analysis, the sample was introduced into the source at 250° C.

The signals received from the mass spectrometer revealed that residue (6) essentially consisted of a mixture of compounds each having the formula (I):

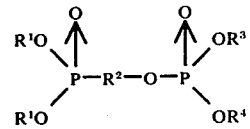
(I)

wherein, $R^1$ is $-C_2H_5$ and $R^2$ is $-C_2H_4-$, with $R^3$ and $R^4$ being different in each compound as follows:

a) $R^3 = R^4 = -CH_2-CH_2Cl$ (mass=386)

b) $R^3$ is $-CH_2-CH_2-Cl$ and (mass=488)

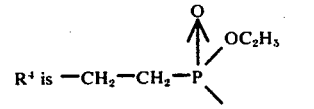

c) 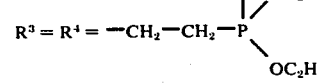 (mass=590)

d) $R^3$ is $-CH_2-CH_2Cl$ and (mass=572)

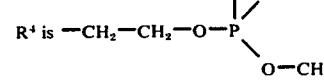

e) $R^3$ is $-CH_2-CH_2Cl$ and

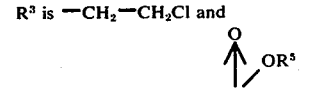

wherein $R^5$ is $-CH_2-CH_2Cl$ and (mass=674)

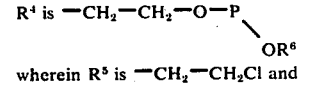

f) $R^3$ is $-CH_2-CH_2Cl$ and

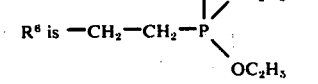

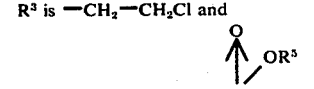
(mass=776)

wherein $R^5 = R^6 = -C_2-CH_2-P(O)(OC_2H_5)_2$ g) 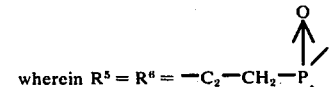 and

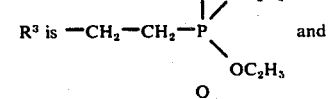

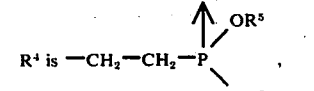
(mass=878).

wherein $R^5 = R^6 = -CH_2-CH_2-P(O)(OC_2H_5)_2$ along with lesser amounts of a not thoroughly identified compound of mass 346, and of a diphosphate having the following structure:

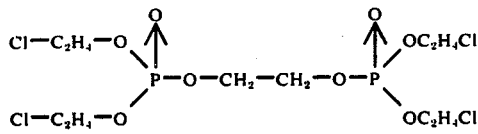

EXAMPLE 2

Following the procedures described in Example 1, two different mixtures of halogenated phosphoric esters were prepared by separately reacting tris($\beta$-chloroethyl)phosphate and triethylphosphite in respective molar ratios of 1:3 and 3:1.

The physico-chemical characteristics of the final products thereby obtained are as follows:

|  | molar ratio | |
|---|---|---|
|  | 1 : 3 | 3 : 1 |
| density at 22° C. | 1.36 | 1.38 |
| refractive index at 20° C. | 1.4675 | 1.4695 |
| Brookfield viscosity (cps) at 18° C. | 580 | 700 |
| Elemental analysis (% by weight) | | |
| carbon | 30.9 | 28.5 |
| hydrogen | 5.8 | 4.9 |
| phosphorus | 16.1 | 15.4 |
| chlorine | 16.4 | 19.4 |
| NMR analysis (%) | | |
| $CH_3$ | 27.42 | 24.7 |
| $P\text{-}CH_2$ | 8.86 | 6.22 |
| $O\text{-}CH_2$ / $CH_2Cl$ | 63.71 | 69.08 |

EXAMPLE 3

The three mixtures of halogenated phosphoric esters described in Examples 1 and 2 were utilized, as non-reacting additives, to impart self-extinguishing characteristics to flexible foamed polyurethanes. For this purpose, the following starting formulation was employed:

| Component | Parts by weight |
|---|---|
| polyether-polyol (a) | 100 |
| flame-proofing additive (b) | variable amounts (see Table) |
| silicone DC 190 (c) | 1.3 |
| 1,4-diazadicyclo(2.2.2) octane at 33% by weight (d) | 0.15 |
| dimethyl ethanolamine | 0.25 |
| tin octoate | 0.25 |
| water | 4.5 |
| trichloro-fluoro methane | 4 |
| toluene diisocyanate (e) | 53.6 |

(a) A commercially available product of Montedison S.p.A., having a molecular weight around 3500 and a OH number of about 47, known as Glendion FG 3501®.
(b) The concentration with respect to the polyol and the type of flame-extinguishing additive are reported in Table I relating to the combustion tests according to ASTM D 1692/68.
(c) Trademark of Dow Corning.
(d) A commercially available product of Houdry Process Corp., known as DABCO 33LV®.
(e) A commercially available product of Montedison S.p.A., consisting of a mixture of 80% by weight of 2,4-toluene diisocyanate and 20% by weight of 2,6-toluene diisocyanate, known as TEDIMON 80®.

The equivalent ratio between the NCO groups and total active hydrogens was equal to 1.05.

The polyurethane was prepared as follows:

The polyol-polyether was directly added to all the other components, except the toluene diisocyanate and the tin octoate.

After mixing for 30 seconds by means of a blade stirrer rotating at 3500 r.p.m., and after having added additional trichlorofluoromethane to make up for loss thereof due to evaporation, the tin octoate and, immediately afterwards, the toluene diisocyanate were added.

After mixing for 4–5 seconds, the whole mass was poured into a 20 × 20 × 20 cm. open mold thoroughly lined with polyethylene coated paper. At the conclusion of the foaming process, after about 2 minutes, the mold was placed into an oven at 110° C. and left therein for 10 minutes, whereupon the product was allowed to undergo complete ageing for a week before being used. A flexible foamed polyurethane having a density of 23 kg./m³ was thereby obtained.

A portion of the polyurethane so prepared was cut into specimens having the dimensions: 15.2 × 5.1 × 1.3 cm. (suited to the combustion test according to ASTM D 1692/68).

The following Table I shows the results obtained from the combustion, according to ASTM D 1692, of various samples of the flexible foamed polyurethane, (prepared as specified above) to which have been added flame-proofing compounds (conventional compounds for comparison and the halogenated phosphoric esters according to the invention) in different amounts. The combustion tests were carried out on non-aged specimens as well as on dry-aged specimens according to ASTM D 2406/68.

TABLE I

| Test No. | Additive Type | Parts by weight per 100 parts of polyols | % by weight chlorine in foam | % by weight phosphorus in foam | Combustion tests according to ASTM D 1692/68 | | | | Remarks |
|---|---|---|---|---|---|---|---|---|---|
|  |  |  |  |  | Combustion rate cm./min. | A* | Self-extinguishing power mm. | sec. |  |
| 1 | — | — |  |  | 18 ± 2 | 8/8 | — | — | *In column A the numerator indicates the number of specimens that actually burn, while the denominator indicates the total number of specimens subjected to combustion; the combustion rate, however, is given only for specimens |
| 2(*) | — | — |  |  | 18 ± 3 | 8/8 | — | — |  |
| 3 | (A) | 10 | 1.22 | 0.97 | 12.6 | 1/8 | — | — |  |
| 4 | (A) | 15 | 1.77 | 1.41 | — | — | 79 ± 8 | 46 ± 3 |  |
| 5 | (A) | 20 | 2.29 | 1.82 | — | — | 57 ± 7 | 35 ± 3 |  |
| 6 | (B) | 10 | 1.04 | 0.99 | 12.6 | 4/8 | — | — |  |
| 7 | (B) | 15 | 1.51 | 1.44 | — | — | 87 ± 9 | 55 ± 5 |  |
| 8 | (B) | 20 | 1.95 | 1.87 | — | — | 51 ± 9 | 34 ± 6 |  |
| 9 | (C) | 15 | 1.24 | 1.56 | — | — | 72 ± 16 | 42 ± 6 |  |

TABLE I-continued

| Test No. | Additive Type | Additive Parts by weight per 100 parts of polyols | % by weight chlorine in foam | % by weight phosphorus in foam | Combustion tests according to ASTM D 1692/68 Combustion rate cm./min. | A* | Self-extinguishing power mm. | sec. | Remarks |
|---|---|---|---|---|---|---|---|---|---|
| 10(*) | (A) | 15 | — | — | 16.2 | 3/8 | — | — | that were thoroughly burnt. |
| 11(*) | (A) | 20 | — | — | — | — | 48 ± 11 | 21 ± 3 | |
| 12 | (D) | 15 | 2.46 | 1.42 | — | — | 58 ± 7 | 33 ± 4 | |
| 13(*) | (D) | 15 | — | — | () | () | () | () | |

(*) Combustion tests (ASTM D 1692/68) 2,10,11 and 13 were carried out on dry-aged specimens (22 hours at 140° C. in an air circulation oven) according to standard ASTM D 2406/68.
(**) It was not possible to carry out the combustion tests since all specimens, after being dry-aged, were thoroughly crumbled.

Notes to Table I
(A) Mixture of halogenated phosphoric esters prepared according to Example 2 starting from tris(β-chloroethyl)phosphate and triethylphosphite in a molar ratio of 3:1.
(B) Mixture of phosphoric esters prepared according to Example 2 starting from a molar ratio of 1:3.
(C) Mixture of phosphoric esters prepared according to Example 1 starting from a molar ratio of 1:1.
(D) Commercially available product known as PHOSGARD C 22 R, of Monsanto Chem. Co., having the following general formula:

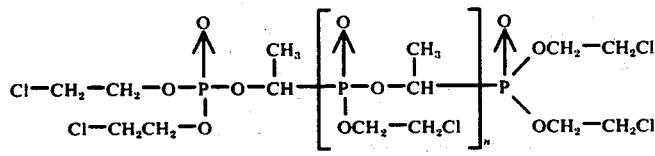

The results set forth in Table I are indicative of the considerable efficiency, as self-extinguishing agents, of the halogenated phosphoric esters according to the invention.

In particular, it can be seen that the halogenated phosphoric esters according to the invention are capable, at levels as low as 10 parts per hundred (Tests 3 and 6), of providing products with good flame self-extinguishing characteristics, and at levels of 15 parts per hundred (Tests 4, 5, 7, 8 and 9) of providing products with excellent self-extinguishing characteristics.

Moreover, and unlike what happens when using conventional type halogenated phosphoric esters, the addition of the halogenated phosphoric esters according to the invention does not cause any mechanical deterioration phenomena (see, by way of comparison, Tests 12 and 13). In addition, it can be seen that samples of foamed polyurethane containing respectively the mixture of halogenated phosphoric esters according to Example 2 (molar ratio = 3:1) and tris(β-chloroethyl)phosphate, dry-aged according to standard ASTM 2406, are subject to a phosphorus loss (in relation to the amount initially present), that is rather low (15%) in the case of the products according to the invention, while it is remarkably high (84%) in the case of tris(β-chloroethyl)phosphate, a known product having a constitution somewhat similar to that of the products according to the present invention.

Finally, it is to be pointed out that the phosphoric esters according to the invention are characterized by the relatively low viscosity values; as a result of which they can be utilized without any difficulty in apparatus ordinarily used for the continuous manufacture of flame-proof flexible foamed polyurethanes.

EXAMPLE 4

The mixture of halogenated phosphoric esters prepared according to example 1 was used to improve the flame-extinguishing properties of an unsaturated polyester based on chlorendic acid, maleic anhydride, propylene glycol and styrene, with a chlorine content of 26.6% by weight.

To this regard, the mixture of halogenated phosphoric esters of example 1 and, by comparison conventional flame-retardants such as triethylphosphate tris(β-chloroethyl)phosphate and tris(dichloropropyl)phosphate were added to the polyester dissolved in styrene and the flame-resistance of the thus obtained unsaturated esters was tested according to the method HLT-15 described in INDUSTRIAL AND ENGINEERING CHEMISTRY VOL. 59 N. 5, May 1967, page 114. The thus obtained results are summarized in the following table.

| Type of additive | Amount of additive in polyester parts % by weight as additive | parts % by weight as phosphorus | parts % by weight as chlorine(*) | Self-extinguishing index HLT-15 points |
|---|---|---|---|---|
| No additive | — | — | — | 40 |
| Triethylphosphate | 3.5 | 0.59 | — | 100 |
| (tris(β-chloroethyl)phosphate | 3.4 | 0.37 | 1.27(*) | 84 |
| tris(dichloroethyl) phosphate | 1.0 | 0.07 | 0.49(*) | 60 |
| | 3.0 | 0.22 | 1.48(*) | 88 |
| Mixture of haloge- | | | | |

-continued

| Type of additive | Amount of additive in polyester | | | Self-extinguishing index HLT-15 points |
|---|---|---|---|---|
| | parts % by weight as additive | parts % by weight as phosphorus | parts % by weight as chlorine(*) | |
| nated phosphoric esters of example 1 | 1 | 0.17 | 0.13(*) | 92 |
| | 2.3 | 0.39 | 0.31(*) | 100 |
| | 3.4 | 0.58 | 0.45(*) | 100 |

(*)This figure is exclusively concerned with the chlorine present in the additive and does not include the one present in the polyester and derived from chlorendic acid.

From the above data, it is clear the superiority of the halogenated esters of the present invention over some of the conventional flame-retardant agents for unsaturated polyesters. More particularly it can be seen that the additives according to this invention when used in amounts of 1% parts by weight are actually capable to yield unsaturated polyesters with flame-extinguishing properties equal to or even higher than those of polyesters added with 3.4 parts by weight of tris(β-chloroethyl)phosphate, with 3 parts by weight of tris(dichloroethyl)phosphate or with 3.5 parts by weight of triethylphosphate as it become evident from the HLT-15 indexes 98 vs. respectively 84,88 and 100.

Variation can, of course, be made without departing from the spirit and scope of the invention.

Having thus described our invention, what we desire to secure by Letters Patent and hereby claim is:

1. A mixture of halogenated phosphoric esters consisting essentially of at least two compounds having the general formula (I):

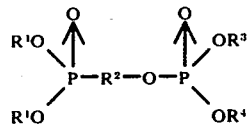

wherein $R^1$ is a $C_1$–$C_3$ alkyl group or an $R^2X$ group as defined hereinbelow, $R^2$ is a $C_2$–$C_3$ alkylene group, and $R^3$ and $R^4$ are independently selected from the group consisting of an —$R^2X$ group, wherein X is a halogen;

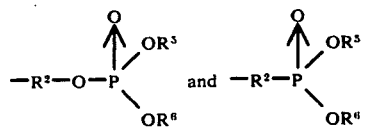

wherein $R^5$ and $R^6$ are independently selected from the group consisting of $R^1$, —$R^2X$ and

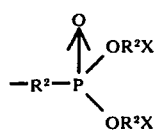

said compounds containing 2 to 6 phosphorus atoms and 0 to 3 halogen atoms per molecule.

2. A mixture according to claim 1, wherein X is chlorine or bromine.

3. A mixture according to claim 2, wherein $R^1$ is $C_2H_5$ and $R^2$ is —$CH_2$—$CH_2$—.

4. A mixture according to claim 3, wherein the principal components thereof are those wherein $R^3$ and $R^4$ have the following meanings:

a) $R^3 = R^4 = $ —$CH_2$—$CH_2Cl$ (mass=386)

b) $R^3$ is —$CH_2$—$CH_2$—Cl and $R^4$ is $-CH_2-CH_2-\overset{O}{\underset{OC_2H_5}{\overset{\uparrow}{P}}}\overset{OC_2H_5}{}$ (mass=488)

c) $R^3 = R^4 = $ —$CH_2$—$CH_2$—$\overset{O}{\underset{OC_2H_5}{\overset{\uparrow}{P}}}\overset{OC_2H_5}{}$ (mass=590)

d) $R^3$ is —$CH_2$—$CH_2Cl$ and $R^4$ is —$CH_2$—$CH_2$—O—$\overset{O}{\underset{O-CH_2-CH_2Cl}{\overset{\uparrow}{P}}}\overset{O-CH_2-CH_2Cl}{}$ (mass=572)

e) $R^3$ is —$CH_2$—$CH_2Cl$ and $R^4$ is —$CH_2$—$CH_2$—O—$\overset{O}{\underset{OR^6}{\overset{\uparrow}{P}}}\overset{OR^5}{}$ wherein $R^5$ is —$CH_2$—$CH_2Cl$ and $R^6$ is —$CH_2$—$CH_2$—$\overset{O}{\underset{OC_2H_5}{\overset{\uparrow}{P}}}\overset{OC_2H_5}{}$ (mass=674)

f) $R^3$ is —$CH_2$—$CH_2Cl$ and $R^4$ is —$CH_2$—$CH_2$—O—$\overset{O}{\underset{OR^6}{\overset{\uparrow}{P}}}\overset{OR^5}{}$, wherein $R^5 = R^6 = $ —$C_2$—$CH_2$—$\overset{O}{\underset{OC_2H_5}{\overset{\uparrow}{P}}}\overset{OC_2H_5}{}$ (mass=776)

g) $R^3$ is —$CH_2$—$CH_2$—$\overset{O}{\underset{OC_2H_5}{\overset{\uparrow}{P}}}\overset{OC_2H_5}{}$ and $R^4$ is —$CH_2$—$CH_2$—$\overset{O}{\underset{OR^6}{\overset{\uparrow}{P}}}\overset{OR^5}{}$, wherein $R^5 = R^6 = $ —$CH_2$—$CH_2$—$\overset{O}{\underset{OC_2H_5}{\overset{\uparrow}{P}}}\overset{OC_2H_5}{}$ (mass=878).

5. A process for preparing the mixture of claim 2, comprising reacting a trialkylphosphite of the formula $P(OR^1)_3$ and a tris(haloalkyl)phosphate of the formula $PO(OR^2X)_3$ wherein $R^1$, $R^2$ and $X$ are as defined in claim 2.

6. A process according to claim 5, wherein the molar ratio of the trialkylphosphite to the tris(haloalkyl)phosphate is between 1:3 and 3:1 and the reaction is effected for 2–24 hours at a temperature of 140°–220° C.

7. A flexible foamed polyol based polyurethane having incorporated therein from 1 to 25 parts by weight, per 100 parts by weight of polyol, of a mixture of halogenated phosphoric esters according to claim 1.

* * * * *

UNITED STATES PATENT OFFICE
CERTIFICATE OF CORRECTION

Patent No. 4,025,468                     Dated 5/24/77

Inventor(s) Mario Modena and Roberto Bisel

It is certified that error appears in the above-identified patent and that said Letters Patent are hereby corrected as shown below:

Column 5, line 55: "spctrograph" should read -- spectrograph --.

Column 6, lines 46-49:

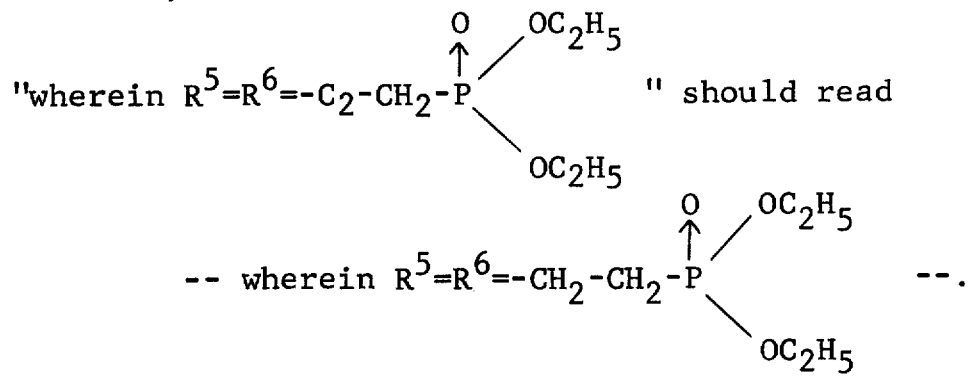

Columns 11-12, column 3, in the heading of the table:
" parts %  "    should read  --  parts %   --.
  by weight                       by weight
 as phosph0-                     as phospho-
    rus                              rus

UNITED STATES PATENT OFFICE
CERTIFICATE OF CORRECTION

Patent No. 4,025,468  Dated 5/24/77

Inventor(s) Mario Modena and Roberto Bisel

It is certified that error appears in the above-identified patent and that said Letters Patent are hereby corrected as shown below:

Column 12, lines 50-54:

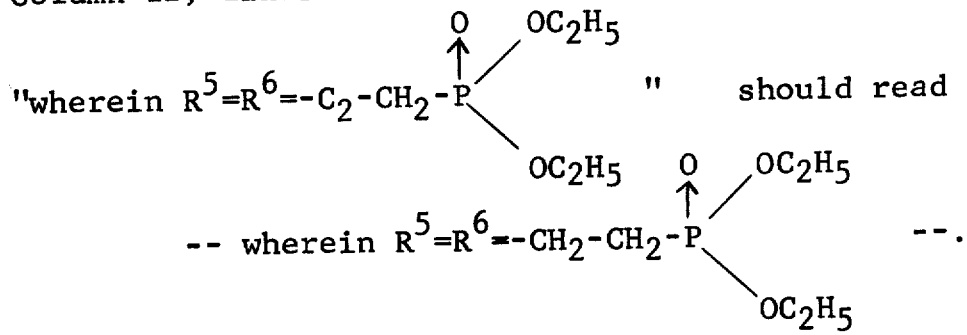

Signed and Sealed this twenty-third Day of August 1977

[SEAL]

Attest:

RUTH C. MASON
Attesting Officer

C. MARSHALL DANN
Commissioner of Patents and Trademarks